(12) United States Patent
Chen et al.

(10) Patent No.: US 9,844,315 B2
(45) Date of Patent: Dec. 19, 2017

(54) SIGNAL NORMALIZATION AMONG MULTIPLE OPTICAL COHERENCE TOMOGRAPHY DEVICES

(71) Applicant: University of Pittsburgh—Of the Commonwealth System of Higher Education, Pittsburgh, PA (US)

(72) Inventors: Chieh-Li Chen, Seattle, WA (US); Hiroshi Ishikawa, Allison Park, PA (US); Joel Steven Schuman, Pittsburgh, PA (US); Chaim-Gadi Wollstein, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 149 days.

(21) Appl. No.: 14/877,178

(22) Filed: Oct. 7, 2015

(65) Prior Publication Data

US 2016/0100755 A1 Apr. 14, 2016

Related U.S. Application Data

(60) Provisional application No. 62/061,508, filed on Oct. 8, 2014, provisional application No. 62/092,058, filed on Dec. 15, 2014.

(51) Int. Cl.
*G06K 9/00* (2006.01)
*A61B 3/00* (2006.01)
(Continued)

(52) U.S. Cl.
CPC ............ *A61B 3/0025* (2013.01); *A61B 3/102* (2013.01); *G06K 9/0061* (2013.01); *G06T 5/002* (2013.01);
(Continued)

(58) Field of Classification Search
CPC .................. A61B 3/0025; A61B 3/102; G06T 2207/10101; G06T 2207/30041;
(Continued)

(56) References Cited

U.S. PATENT DOCUMENTS

2016/0097632 A1* 4/2016 Sumiya ............. G01B 9/02091
356/479

FOREIGN PATENT DOCUMENTS

WO WO 2011/063220 A2 5/2011

OTHER PUBLICATIONS

Chieh-Li Chen et al., "Individual A-Scan Signal Normalization Between Two Spectral Domain Optical Coherence Tomography Devices," *Multidisciplinary Ophthalmic Imaging*, vol. 54, No. 5, pp. 3463-3471 (2013).

(Continued)

*Primary Examiner* — Tom Y Lu
(74) *Attorney, Agent, or Firm* — Foley & Lardner LLP

(57) ABSTRACT

The present disclosure is directed to systems and methods for normalizing an image of an eye among multiple optical coherence tomography (OCT) devices. The system can receive an OCT image and generate a normalized OCT image. The system is configured to normalize a sample density of the received image, normalize an amount of noise using a suitable noise reduction technique, normalize a distribution of signal amplitudes of the image, and then normalize a signal quality of the image. The resulting normalized image of the eye can then be used in the comparison among OCT images taken from multiple OCT devices.

18 Claims, 8 Drawing Sheets

(51) Int. Cl.
*G06T 7/00* (2017.01)
*A61B 3/10* (2006.01)
*G06T 5/00* (2006.01)

(52) U.S. Cl.
CPC ............ *G06T 5/009* (2013.01); *G06T 7/0012* (2013.01); *G06T 2207/10101* (2013.01); *G06T 2207/30041* (2013.01)

(58) Field of Classification Search
CPC ......... G06T 7/0012; G06T 2207/10004; G06T 5/002; G06T 5/009; G06T 7/0081; G06K 9/0061; G06K 9/6215; H02J 50/12; H02J 50/80; H02J 7/025
See application file for complete search history.

(56) References Cited

OTHER PUBLICATIONS

Chieh-Li Chen et al., "Signal Normalization Reduces Systematic Measurement Differences Between Spectral-Domain Optical Coherence Tomography Devices," *Multidisciplinary Ophthalmic Imaging*, vol. 54, No. 12, pp. 7317-7322 (2013).

Ishikawa et al., "High Dynamic Range Imaging Concept-Based Signal Enhancement Method Reduced the Optical Coherence Tomography Measurement Variability," *Multidisciplinary Ophthalmic Imaging*, vol. 54, No. 1, pp. 836-841 (2013).

\* cited by examiner

SIGNAL NORMALIZATION AMONG MULTIPLE OPTICAL COHERENCE TOMOGRAPHY DEVICES

CROSS-REFERENCE TO RELATED APPLICATIONS

This application claims priority to U.S. Provisional Patent Application No. 62/061,508, filed on Oct. 8, 2014, and titled "SIGNAL NORMALIZATION AMONG MULTIPLE OPTICAL COHERENCE TOMOGRAPHY DEVICES," and U.S. Provisional Patent Application No. 62/092,058, filed on Dec. 15, 2014, and titled "OPTICAL COHERENCE TOMOGRAPHY IMAGE ENHANCEMENT USING A NOVEL HISTOGRAM MATCHING BASED IMAGE PROCESSING," both of which are herein incorporated by reference in their entirety.

FIELD OF THE DISCLOSURE

This disclosure generally relates to systems and methods for normalizing an optical coherence tomography image.

BACKGROUND OF THE DISCLOSURE

Optical coherence tomography (OCT) is an ocular imaging technique used in clinical ophthalmological care. OCT uses a broad-bandwidth light source to generate cross-sectional, sub-surface images of the eye. There are many commercially available OCT devices. The different OCT devices provide a wide variety of options in terms of cost, scan protocols, image processing, and presentation. However, the diversity in devices can present challenges when comparing images generated by different devices, as the ocular images generated by the different devices show variations unique to the devices, rather than to the imaged eye.

Signal normalization techniques are described, for example, in Ishikawa et al., "High Dynamic Range Imaging Concept-Based Signal Enhancement Method Reduced the Optical Coherence Tomography Measurement Variability," IONS, 54(1):836-841 (2013); Chen et al., "Signal Normalization Reduces Systemic Measurement Differences Between Spectral-Domain Optical Coherence Tomography Devices," *IOVS*, 54(12):7317-7322 (2013); Chen et al., "Individual A-Scan Signal Normalization Between Two Spectral Domain Optical Coherence Tomography Devices," *IOVS*, 54(5):3463-3471 (2013); and WO 2011/063220.

There is a need in the art for methods of normalizing images of generated from different OCT devices. The present invention satisfies this need.

SUMMARY OF THE DISCLOSURE

According to one aspect of the disclosure, a method for normalizing an image of an eye among multiple optical coherence tomography devices includes, in the following specified sequence, (a) normalizing a sample density, (b) normalizing an amount of noise using a suitable noise reduction technique, (c) normalizing a signal of amplitude, and (d) normalizing a signal quality. The sequence of steps results in a normalized image of the eye among multiple optical coherence tomography devices.

In some implementations, the method can also include receiving a first pixmap that includes a first plurality of pixels. The first pixmap can represent an image of an eye and have a first sample density. The method can also include generating a second pixmap comprising a second plurality of pixels by resampling the first plurality of pixels at a predetermined sampling density. In some implementations, the method can also include filtering the second pixmap to remove at least a portion of a noise signal in the second pixmap.

The method can also include rescaling a distribution of signal amplitudes of the filtered second pixmap such that the distribution of signal amplitudes spans a substantial portion of a dynamic range of the filtered second pixmap. The method can also include normalizing the distribution of signal amplitudes of the rescaled, filtered second pixmap. In some implementations, resampling the first sample density includes up scaling the first sample density.

In some implementations, the method can include normalizing the distribution of signal amplitudes by applying a high-dynamic range (HDR) process to the second pixmap. The HDR process can include dividing the second plurality of pixels into a low level signal, a medium level signal, and a high level signal. The HDR process can also include linearly scaling each of the low level signal, the medium level signal, and the high level signal between a lowest and a highest value within each of the respective signals, and then combining the linearly scaled low level, medium level, and high level signals.

In some implementations, normalizing the distribution of signal amplitudes further comprises applying a histogram matching (HM) process to the second pixmap. The HM process can comprise (i) dividing the second pixmap into a top portion and a bottom portion; (ii) generating a first histogram from the top portion of the second pixmap; (iii) mapping the first histogram to a top reference histogram; (iv) generating a second histogram from the bottom portion of the second pixmap; and (v) mapping the second histogram to a bottom reference histogram. In certain implementations, the second pixmap is divided along a line representing a lowest intensity between an outer plexiform layer and an external limiting membrane of the eye.

In some implementations, rescaling the distribution of signal amplitudes can include generating a histogram of pixel intensities of the second plurality of pixels; setting a portion of the second plurality of pixels below or equal to about 66% of the histogram to about 0; and distributing a portion of the second plurality of pixels between about 66% and about 99% of the histogram across the substantial portion of the dynamic range. In other embodiments, the portion of the second plurality of pixels is set below or equal to about 65%, below or equal to about 60%, below or equal to about 55%, below or equal to about 50%, below or equal to about 45%, below or equal to about 40%, below or equal to about 35%, below or equal to about 30%, below or equal to about 25%, or below or equal to about 20% of the histogram to 0. In yet other embodiments, the portion of the second plurality of pixels is distributed between about 70% and about 99%, between about 75% and about 99%, between about 80% and about 99%, between about 85% and about 99%, between about 90% and about 99%, and between about 95% and about 99% of the histogram across the substantial portion of the dynamic range.

In some implementations, the noise signal is a high frequency noise signal. Filtering the second pixmap can include applying a mask to the second pixmap. The mask can include a smoothed copy of the second pixmap.

According to another aspect of a disclosure, a system for normalizing an image of an eye among multiple optical coherence tomography devices can comprise one or more data processors and one or more storage devices storing instructions. When executed, the instructions cause the one or more data processors to receive a first pixmap including a first plurality of pixels. The first pixmap represents an image of an eye and having a first sample density. The instructions also cause the one or more data processors to generate a second pixmap including a second plurality of pixels. The second pixmap is generated by resampling the first plurality of pixels at a predetermined sampling density. The instructions also cause the one or more data processors to filter the second pixmap to remove at least a portion of a noise signal in the second pixmap, and to rescale a distribution of signal amplitudes of the filtered second pixmap such that the distribution of signal amplitudes spans a substantial portion of a dynamic range of the filtered second pixmap. The instructions further cause the one or more data processors to normalize the distribution of signal amplitudes of the rescaled, filtered second pixmap, and then provide a normalized image of the eye responsive to the normalized distribution of signal amplitudes.

In some implementations, the instructions further cause the one or more data processors to normalize the distribution of signal amplitudes by applying a high-dynamic range (HDR) process to the second pixmap. The HDR process can further include dividing the second plurality of pixels into a low level signal, a medium level signal, and a high level signal. The HDR process can also include linearly scaling each of the low level signal, the medium level signal, and the high level signal between a lowest and a highest value within each of the respective signals. The HDR process may further include combining the linearly scaled low level, medium level, and high level signals.

In some implementations, the instructions further cause the one or more processors to normalize the distribution of signal amplitudes by applying a histogram matching (HM) process to the second pixmap. The HM process can comprise (i) dividing the second pixmap into a top portion and a bottom portion; (ii) generating a first histogram from the top portion of the second pixmap; (iii) mapping the first histogram to a top reference histogram; (iv) generating a second histogram from the bottom portion of the second pixmap; and (v) mapping the second histogram to a bottom reference histogram.

In some implementations, the instructions further cause the one or more processors to divide the second pixmap along a line representing a lowest intensity between an outer plexiform layer and an external limiting membrane of the eye.

The instructions can also cause the one or more processors to rescale the distribution of signal amplitudes by (i) generating a histogram of pixel intensities of the second plurality of pixels; (ii) setting a portion of the second plurality of pixels below about a 66 percentile of the histogram to 0; and (iii) distributing a portion of the second plurality of pixels between about a 66 percentile and about a 99 percentile of the histogram across the substantial portion of the dynamic range. In other embodiments, the portion of the second plurality of pixels is set below about 65%, below about 60%, below about 55%, below about 50%, below about 45%, below about 40%, below about 35%, below about 30%, below about 25%, or below about 20% of the histogram to 0. In yet other embodiments, the portion of the second plurality of pixels is distributed between about 70% and about 99%, between about 75% and about 99%, between about 80% and about 99%, between about 85% and about 99%, between about 90% and about 99%, and between about 95% and about 99% of the histogram across the substantial portion of the dynamic range.

In some implementations, the noise signal is a high frequency noise signal. The noise may be filtered by applying a mask to the second pixmap. The mask can include a smoothed copy of the second pixmap. In some implementations, the instructions further cause the one or more processors to resample the first sample density by up scaling the first sample density.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings.

DETAILED DESCRIPTION

Figure 1A:
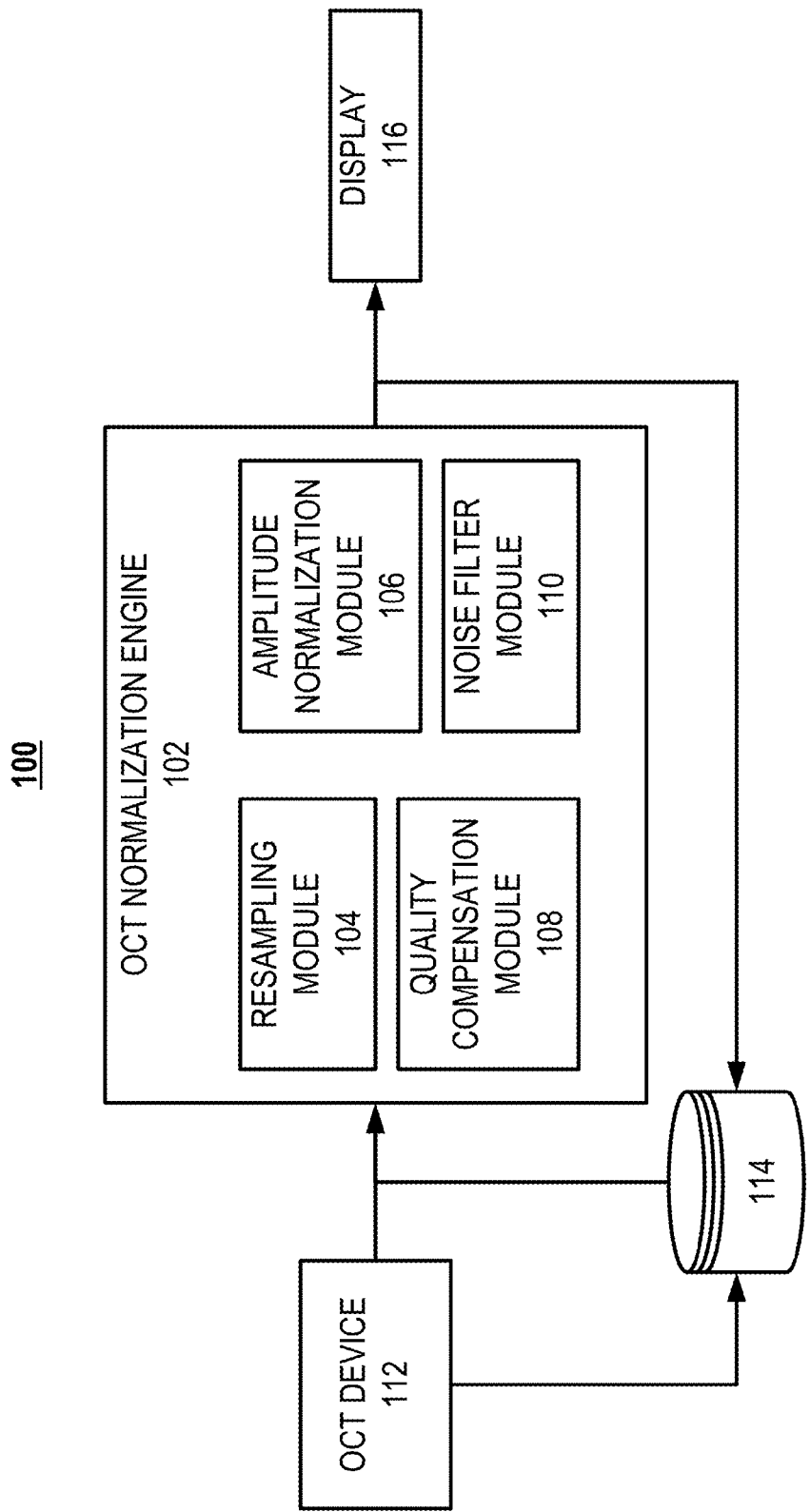
FIG. 1A illustrates a block diagram of an example system for normalizing an OCT image.

The various concepts introduced above and discussed in greater detail below may be implemented in any of numerous ways, as the described concepts are not limited to any particular manner of implementation. Examples of specific implementations and applications are provided primarily for illustrative purposes.

The growing diversity of available OCT devices can result in an equally growing diversity of OCT signal characteristics. The inconsistent signal characteristics can affect both quantitative analysis and qualitative assessment of a patient's eye. For example, systematic measurement differences and discrepancies in image appearance can be observed when scanning the same eye, from the same subject, but with different OCT devices. These differences can pose serious and significant clinical challenges when comparing OCT data measurements from different devices directly, and can prohibit the collection of long-term data of the patient's eye.

In addition to complications generated by growing diversity of available OCT devices, variables such as disease state and age of a patient, can generate OCT images with a diverse set of OCT signal characteristics. In some implementations, these variables can result in a reduced signal strength (SS) of the OCT image. A reduction in SS can make it difficult for clinicians (or automated software) to properly analyze the OCT image to, for example, measure the retinal nerve fiber layer (RNFL) thickness. The reduction in SS can also increase the variability of these measurements. For example, a measured thinning of the RNFL may be from a reduced SS rather than a true pathological thinning of the RNFL. This variability can pose serious and significant clinical challenges when comparing OCT data measurements over time, and can prohibit the collection of long-term data of a patient's eye.

In general, the present disclosure discusses a fully automated signal normalization method that can reduce the signal characteristic variations between OCT images taken with different OCT devices and convert the different OCT images into a standard data format. The systems and methods described herein can normalize four perspectives of the OCT image: (1) sampling density, (2) the amount of noise in the signal, (3) the data dynamic range of the image, and (4) the image quality of the image. In general, the method of normalization described herein processes the OCT image by iteratively improving the above four perspectives, which in general are ordered from least to most complex image processing techniques. Most significantly, the systems and methods described herein can resolve the signal characteristics variability to enable inter-OCT device comparison of OCT images.

The methods of the invention were surprising as it was unexpectedly found that performing the steps in a different order does not result in signal normalization. In particular, while steps (1)-(4) are in general are ordered from least to most complex image processing techniques, when the techniques are rigidly ordered from least to most complex, signal normalization does not occur. Specifically, step (4) is actually more complex than step (3). However, when the sequence of step (3) and (4) is reversed, signal normalization does not result.

In some implementations, the system and methods described herein can calibrate the differences in intensity contrast when capturing images with different cameras, image acquisition equipment, settings, and different light sources. By shaping an input image histogram to a reference histogram, the systems and methods described herein can compensate for the differences in intensity and image contrast. While described primarily in relation to OCT techniques, the system and methods described herein can be used with other imaging modalities, such as, but not limited to, positron emission tomography (PET), single photon emission computed tomography (SPECT), and magnetic resonance imaging (MRI).

FIG. 1A illustrates a block diagram of an example system 100 for normalizing an OCT image. The system 100 includes an OCT normalization engine 102 (also referred to simply as a normalization engine 102). The normalization engine 102 can include a resampling module 104, an amplitude normalization module 106, a quality compensation module 108, and a noise filter module 110. The normalization engine 102 can receive OCT images directly from an OCT device 112 or from a database 114. Responsive to normalizing an OCT image, the normalization engine 102 can output the normalized image to a display 116 or save the image back to the database 114.

The system 100 can include one or more OCT devices 112 that generate the OCT images normalized by the normalization engine 102. In some implementations, the OCT device 112 is a device that can measure the retinal thickness and/or the retinal nerve fiber layer thickness. The OCT device 112 can be any type of OCT device that generates an OCT image. For example, the OCT device 112 can be a Cirrus HD-OCT. The Cirrus HD-OCT may generate three-dimensional (3-D) cube data of the retina, and can collect 200×200 sampling points from a 6×6 mm² area centered on the optic disc and 1024 sampling points within a 2.0 mm axial scan depth. Another example OCT device 112 can include the RTVue OCT. An RTVue OCT image may include 1019 A-scans and 768 samplings along each A-scan for a 2.3 mm axial scan depth. In some implementations, the images generated by the OCT device 112 are referred to generally as pixmaps (or pixel maps), which can include a map of the pixels that are used to generate the OCT image. Each of the pixels may be stored in one or more bytes. In some implementations, a number of image types can be generated from the pixmap. For example, each column (or row) of the pixmap may store the data for one A-scan. A plurality of A-scans stored in the columns (or rows) can be combined to create a cross-sectional image (or B-scan image). An en face image can be generated by integrating the intensity information along the axial direction of the A-scans.

The system 100 can also include a database 114 for the storage and retrieval of the pixmaps generated by the OCT device 112. The database 114 may include one or more hard disk drives or redundant arrays of independent disks for storing pixmaps, processor executable instructions, and other data. Example databases 114 can include one or more hard disk drives (HDD); one or more optical drives including CD drives, DVD drives, or BLU-RAY drives; one or more solid-state drives (SSD); one or more USB flash drives; or any other device suitable for storing data. In some implementations, the database 114 may be non-volatile, mutable, or read-only. In some implementations, the database 114 may be connected to the other components of the system 100 via a network (e.g., a local area network, the internet, a cellular network, or a wide area network). The database 114 may be a component of the normalization engine 102. For example, the database 114 may be a hard drive housed within the normalization engine 102.

The system 100 can also include a display 116 for displaying the normalized image (or other images) to a user of the system 100. The display 116 can be any type of computer or other monitor. The display may be color or black and white. Example displays 116 can include, but are not limited to, liquid crystal displays (LCDs) and active-matrix organic light-emitting diode (AMOLED) displays. In some implementations, the display 116 may be connected to the normalization engine 102 over a network. For example, the normalized image may be provided to a user's tablet computer or other hand held device for display over a network.

The system can also include a normalization engine 102 for the normalization of OCT images. The normalization engine 102 can include an application, program, library, service, task, or any type and form of executable instructions to normalize images such that the images generated by different OCT devices 112 can be compared. In some implementations, the normalization engine 102 normalizes the images to a predetermined normalization level. In other implementations, a first reference image is provided and then the subsequent images are normalized to the first reference image. As described above, the normalization engine 102 can include a resampling module 104, an amplitude normalization module 106, a quality compensation module 108, and a noise filter module 110. Each of these modules is described in greater detail in relation to FIGS. 2-7.

As an overview, the resampling module 104 of the normalization engine 102 can be designed, constructed, and/or configured to resample a received first pixmap to generate a second pixmap. The second pixmap is generated to have a predetermined sampling density. For example, a pixmap from a first OCT device 112 may include 1024 pixels while a pixmap from a second OCT device 112 may only include 640 pixels. The pixmaps may be up-sampled or down-sampled. Resampling a pixmap to a predetermined sampling density can allow different pixmaps to be aligned to a reference point, such as the inner limiting membrane (ILM) or the inner-most border of the retina. This can enable a pixel-by-pixel comparison between the two images.

Continuing the overview of the normalization engine 102, the normalization engine 102 can also include a noise filter module 110. The noise filter module 110 can be designed, constructed, and/or configured to filter the pixmap to remove a portion of a noise single in the pixmap. In some implementations, speckle noise is a component of an OCT image. The interference that can cause the noise in the signal can be from the backscattering of waves with the same frequency but with different phases and amplitudes. The interference can present on the image as speckles with a granular pattern on the OCT cross-sections. Speckle noise can degrade the quality of acquired images, masking actual target signals, and causing difficulties in qualitative assessment as well as quantitative analysis. Speckle noise also results in the variability in OCT signal between OCT images. In some implementations, the noise filter module 110 is configured to remove the noise and maintain as much of the true retinal structural data without substantially blurring the fine-textured tissue structure regions of the eye (e.g., within retinal layers). In some implementations, blurring an OCT image to remove noise can affect qualitative assessment.

The normalization engine 102 can also include an amplitude normalization module 106. The amplitude normalization module 106 can be designed, constructed, and/or configured to rescale a distribution of signal amplitudes of a pixmap. When rescaled, the distribution of the signal amplitudes can span a substantial portion of the dynamic range of the pixmap. A substantial portion of the dynamic range can include a range that includes between about 80% and about 100% of the dynamic range, between about 85% and about 100% of the dynamic range, between about 90% and about 100% of the dynamic range, or between about 95% and about 100% of the dynamic range.

The normalization engine 102 can also include a quality compensation module 108. In general the quality compensation module 108 can be designed, constructed, and/or configured to normalize the distribution of the signal amplitudes of an OCT image. In some implementations, the quality compensation module 108 may perform high-dynamic range processing or histogram matching on the input image to improve the image quality.

Figure 1B:
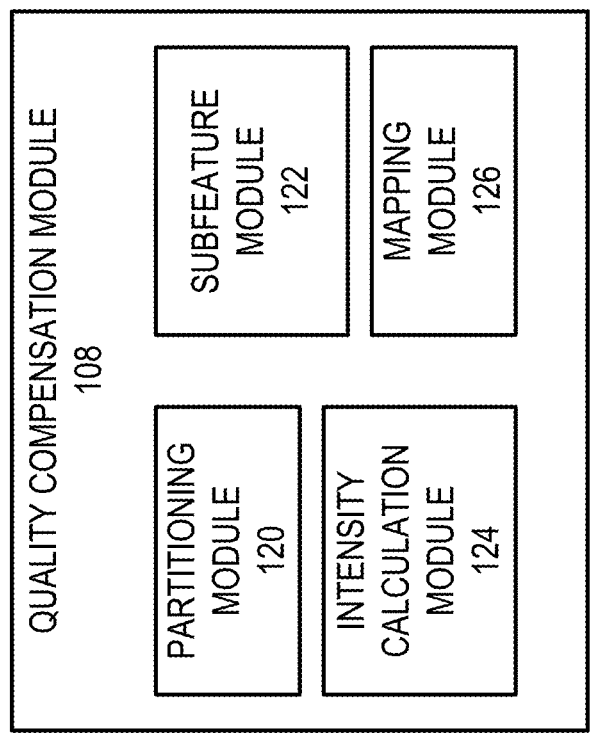
FIG. 1B illustrates a block diagram of the quality compensation module from the system illustrated in FIG. 1A in greater detail.

FIG. 1B is a block diagram of the quality compensation module 108 in greater detail. The quality compensation module 108 can include a partitioning module 120, a sub-feature calculation module 122, an intensity calculation module 124, and a mapping module 126.

As an overview, the partitioning module 120 of the quality compensation module 108 can be designed, constructed, and/or configured to partition a received OCT image. In some implementations, the partitioning module 120 partitions an OCT image (e.g., a B-scan image) into an upper and lower portion. The partitioning module 120 can include segmentation software that divides the B-scan image into the upper and the lower portion along a predetermined anatomical boundary. For example, the upper and the lower portion of the B-scan may be generated by dividing the B-scan along the valley of the OCT signal amplitude where the amplitude is the lowest between the outer plexiform layer (OPL) and the external limiting membrane. The upper portion can include one or more of the top half of the vitreous body, the RNFL, the ganglion cell layer (GCL), the inner plexiform layer (IPL), and/or the OPL. The lower portion can include one or more of the outer nuclear layer, the inner and the outer segment (IS/OS), the retinal pigment epithelium (RPE), and/or the region below the RPE. In some implementations, the upper portion and the lower portion each include about half of the pixels contained within the B-scan. In other embodiments, the upper portion and/or the lower portion each include about 40%, about 50%, about 60%, about 70%, about 80%, or about 90% of the pixels contained within the B-scan. The B-scan may be cropped or padded so that the proportions of the actual retinal signal are consistent across different images when the B-scan is divided along the line.

The quality compensation module 108 can also include an intensity calculation module 124. The intensity calculation module 124 can be designed, constructed, and/or configured to calculate an intensity histogram of each portion of the histogram partitioned by the partitioning module 120. The histograms of the upper and lower portions can indicate the percentile information at each pixel intensity present in each portion of the partitioned B-scan image. The percentile information at each intensity level can be calculated with:

$$P[i] = \frac{\sum_{x=0}^{i} n_x}{N}, 0 \leq i \leq 255 \quad (1)$$

where P[i] indicates the percentile information at intensity i, and $n_x$ shows the number of pixels having intensity x. N represents the total number of pixels with the region. The dynamic range of the data is from 0 to 255 (for 8-bit data). In some implementations, 12-bit or 16-bit data can be used and the dynamic range is 0-4095 or 0-65535.

The quality compensation module 108 can also include a sub-feature calculation module 122. The sub-feature calculation module 122 can be designed, constructed, and/or configured to calculate a sub-feature of each pixel (or voxel) of the partitioned B-scan image. In some implementations, equation 1, above, treats pixels with the same intensity as a group and may not be able to distinguish pixels with the same intensity. For example, pixels with the same intensity, but from different retinal layers may be binned together in the intensity calculation. This grouping can cause approximation errors due to quantization and rounding. Pixels with the same intensity may be separated with the introduction of one or more sub-features calculated by the sub-feature calculation module 122. The addition of the sub-feature enables each of the bins created for the histograms by equation 1 to be subdivided, which results in improving resolution and improving the histogram shape. The sub-feature can include, but is not limited to, mean intensity of a local neighborhood of pixels, variance of the local neighborhood, differentiation of the local neighborhood, variance of the local neighborhood, maximum or minimum difference of the local neighborhood, standard deviation of the local neighborhood, z-location of the pixel of interest, or a combination thereof. In some implementations, the local neighborhood can be a 3×3, 5×5, 7×7, 9×9, 11×11, or more neighboring of pixels with pixel of interest at the center of the neighborhood. For example, the sub-feature can be the mean intensity of a pixel's 3×3 neighbors. In this example using 8-bit data, each sampling point can have a new intensity value $I_{new}$ represented by:

$$I_{new} = I_{ori} + 256 \times I_{mean} \quad (2)$$

In implementations using 12-bit or 16-bit data, the 256 in equation 2 is replaced with the dynamic range of the data –4096 for 12-bit data or 65536 for 16-bit data.

The quality compensation module 108 can also include a mapping module 126. The mapping module 126 can be designed, constructed, and/or configured to map the intensity histograms generated by the intensity calculation module 124 to reference histograms. For example, based on the percentile information, a mapping matrix can convert the shape of the input histogram from the intensity calculation module 124 to the shape of the respective reference histogram. The mapping matrix may match or reduce the distance in percentile at each intensity on the histograms between reference and input histograms, as shown below:

$$T[i] = j, \text{ if } |P_{in}[i] - P_{ref}[j]| = \min_k |P_{in}[i] - P_{ref}[k]| \quad (3)$$

where T[i] is the resulted mapping matrix, and $P_{in}[i]$ and $P_{ref}[j]$ are the percentile information on the input and reference histograms at intensity i and j, respectively. For each intensity i in the input histogram, a corresponding intensity j in the reference histogram is calculated so that the percentile $P_{in}[i]$ and $P_{ref}[i]$ had a minimal difference. All of the sample points in the input image data with intensity i were then mapped to intensity j to generate the output image data.

Figure 2:
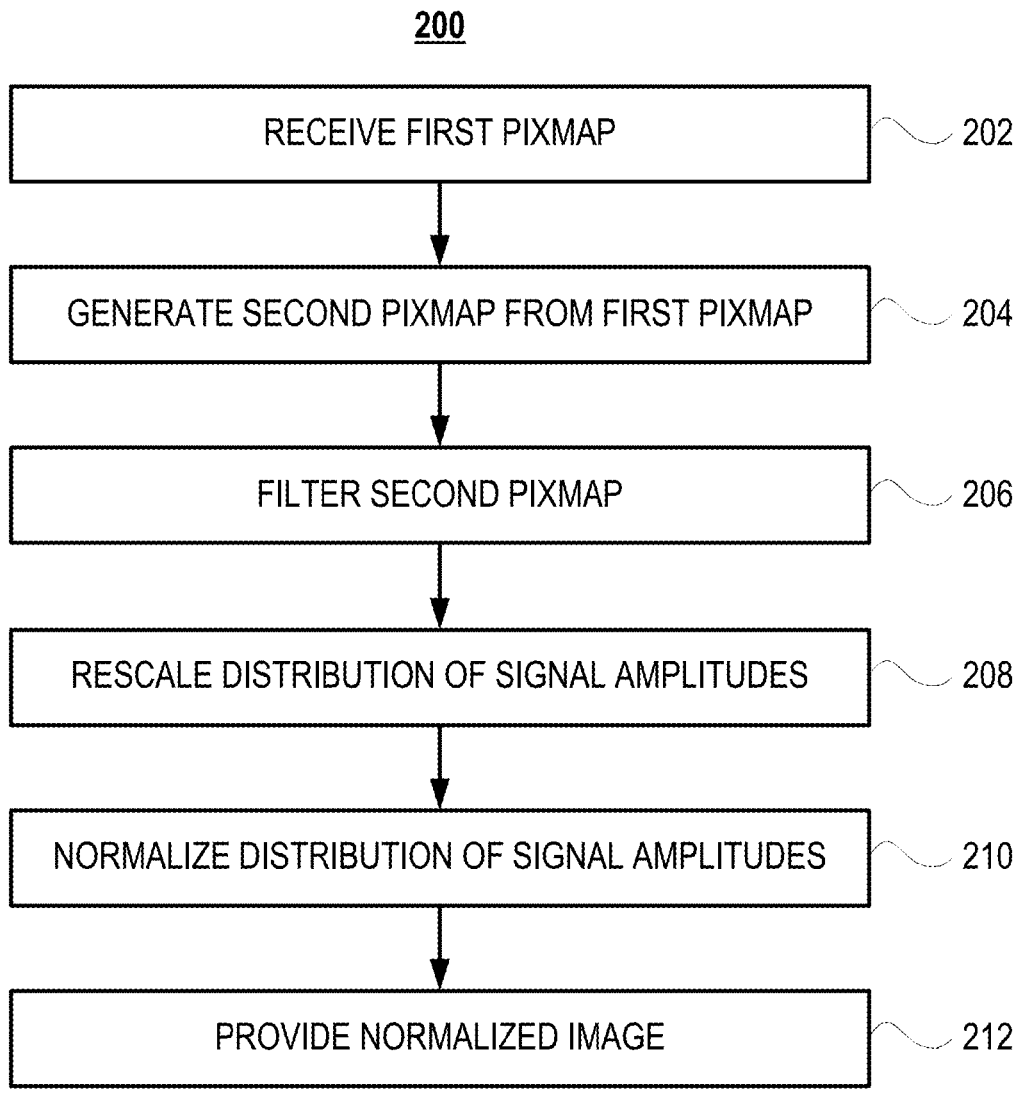
FIG. 2 illustrates a flow diagram of an example method for normalizing an image using the system illustrated in FIG. 1A.

FIG. 2 illustrates a flow diagram of an example method 200 for normalizing an image. The method 200 includes receiving a first pixmap (step 202), and generating a second pixmap from the first pixmap (step 204). The second pixmap is then filtered (step 206). The distribution of the signal amplitudes is then rescaled (step 208). Next, the distribution of signal amplitudes is normalized (step 210), and the normalized image is provided (step 212). In some implementations, performing the method 200 in the above listed order generates substantially better output images when compared to the results of performing the normalization process in a different order.

As set forth above, the method 200 begins with the receipt of a first pixmap (step 202). As described above, the pixmap can be an OCT image of an eye, for example. In some implementations, the first pixmap is received directly from an OCT device and in other implementations the first pixmap can be received from a database. During the method 200, the first pixmap may be stored within the normalization engine 102 (e.g., in RAM of the normalization engine 102) and be transformed through the methods described herein into a normalized pixmap.

Next, a second pixmap is generated (step 204). The second pixmap can be generated by resampling the first pixmap at a predetermined pixel density. For example, the first pixmap may be received and include a first plurality of pixels (e.g., 1024 pixels). Resampling the first pixmap to a predetermined amount of pixels may generate the second pixmap. Continuing the above example, the first pixmap may be down sampled to 512 pixels. In some implementations, the resampling of the first pixmap can be along one or both of the transverse and axial direction. In some implementations, the first pixmap may be resampled to have different sample densities in the traverse and axial direction. In other implementations, the sample density may be up sampled. For example, images with 768, 496, and 640 pixels may be up sampled to include 1024 samples, such that each of the images can be aligned and compared. In some implementations, the pixmaps from different images can be scaled and resampled using the below equation:

$$z_{target} = z \left( \frac{\text{Scan Depth}_{ref}}{N_{ref}} \right) \left( \frac{N_{in}}{\text{Scan Depth}_{in}} \right) \quad (4)$$

where $z_{target}$ indicates the target z index to be sampled for the interpolation, and z is the index in the z direction of the pixel of the given A-scan from the second pixmap. Scan Depth$_{ref}$ and Scan Depth$_{in}$ are the scan depth for the reference data format (e.g., 2.0 mm), and for the input device. $N_{ref}$ and $N_{in}$ are the sampling points for the reference data format, for the input device, respectively. In some implementations, after calculating $z_{target}$, a one-dimensional linear interpolation can be applied to generate a smoothly interpolated A-scan profile.

After generating a second pixmap by resampling the first pixmap, the second pixmap is filtered (step 206). In some implementations, the filter can be any type of image processing that removes the speckle noise component from the second pixmap. For example, the image processing can include, but is not limited to, adaptive filtering, mean filtering, Gaussian filtering, anisotropic diffusion, and wavelet techniques. In some implementations, the filter is designed to preserve the edges in the OCT images (e.g., substantially not blur the image) and be computationally efficient. In some implementations, the filtering step 206 can include applying a two-dimensional mean filter to the pixmap. In some implementations, the kernel size in the axial direction of the mean filter can be a function of the number of pixels in the axial direction. For example, a kernel size of 3×7 (3 in the transverse direction and 7 in the axial direction) can be used for a pixmap with 1024 pixels in the axial direction. In some implementations, a smoothed A-scan can then be used as a mask to selectively remove high signal peaks (e.g., speckle noise) from the second pixmap. For example, the signal intensity at each location of each smoothed A-scan from the second pixmap can be compared to the respective position in the original A-scan from the second pixmap. If the pixel from the original pixmap shows a higher intensity than the counterpart in the mask, the intensity of the original pixel can be adjusted to match the intensity of the mask. Mathematically, this is represented by the below equation:

$$I_{SpR} = \begin{cases} I_R, & \text{if } I_O > I_R \\ I_O, & \text{if } I_O < I_R \end{cases} \quad (5)$$

In equation 5, $I_{SpR}$ is the final intensity of a given pixel after filtering, $I_R$ is the pixel intensity of the given pixel in the mask, and $I_O$ is the pixel intensity of the given pixel in the original image.

Figure 3:
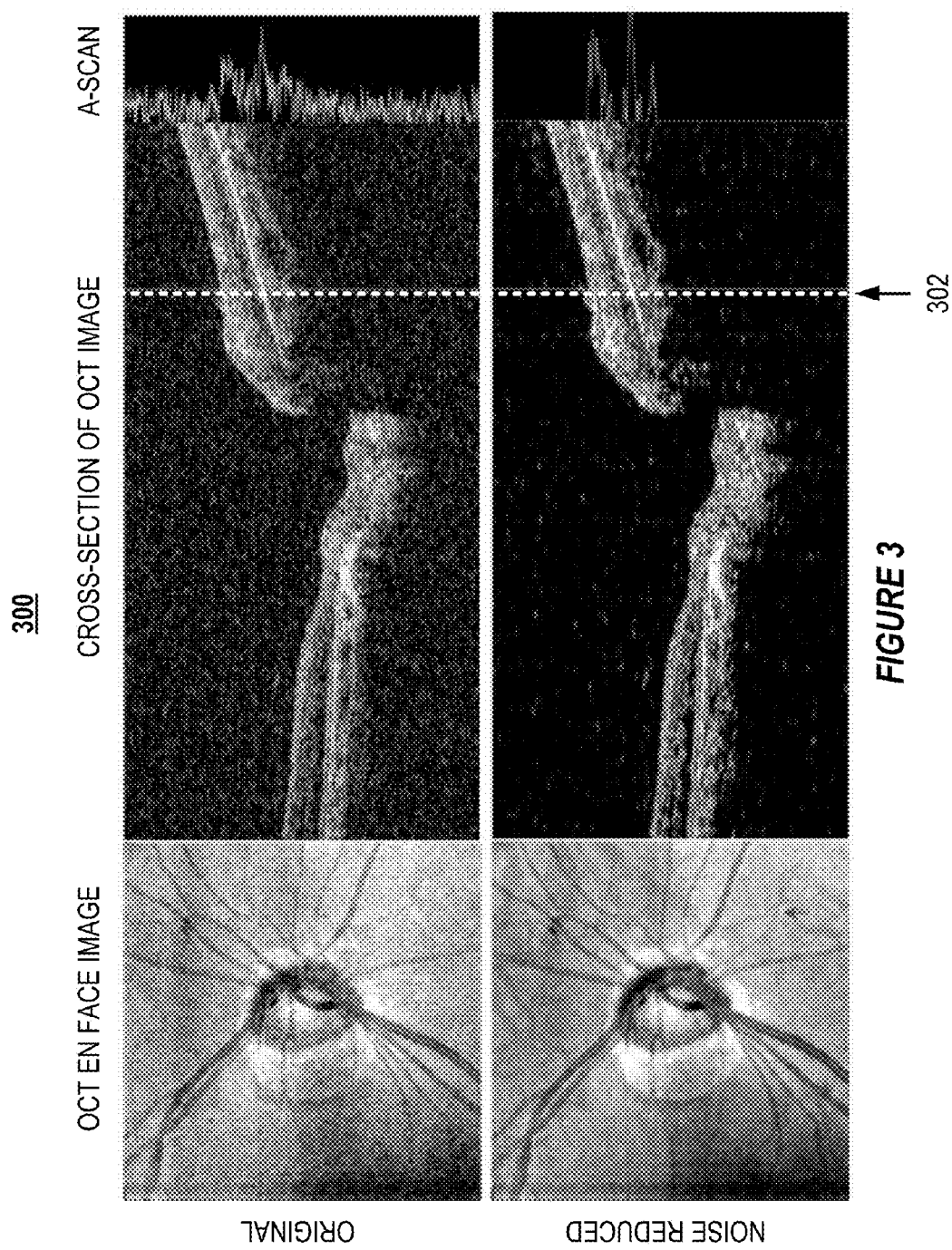
FIG. 3 illustrates a comparison of a non-filtered and filtered OCT image, where the OCT image was filtered according to the example method illustrated in FIG. 2.

FIG. 3 illustrates a comparison 300 of a non-filtered and filtered OCT image. In the top row, and from left to right, the comparison 300 illustrates an original en face image, an original cross-section image (B-scan), and an original A-scan (with the A-scan generated along line 302). In the bottom row, from left to right, the comparison 300 illustrates a noise reduced en face image, a noise reduced cross-section image (B-scan), and a noise reduced A-scan. The original A-scan includes high to moderate signal amplitudes along most of the A-scan length. When a mask is applied and the intensity of each pixel reduced according to equation 5, many of the pixel intensities are reduced to nominal levels, leaving only the anatomical structure of eye. In both the cross-section view and the en face image, the noise is reduced while the sharpness of the image is substantially maintained. For example, the black portions of the noise-reduced cross section are substantially free of speckle noise when compared to the original cross-section image.

Figures 4A, 4B:
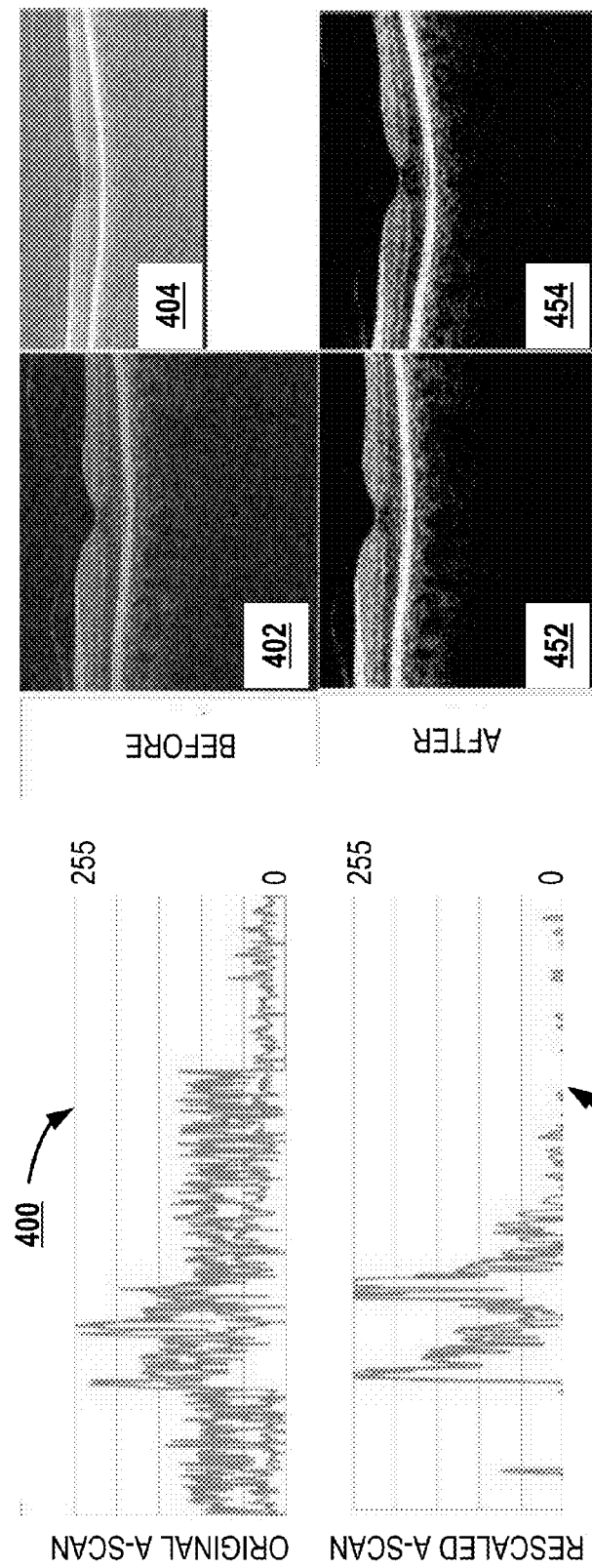
FIG. 4A illustrates an original A-scan and a rescaled A-scan, where the A-scan was rescaled according to the example method illustrated in FIG. 2.
FIG. 4B illustrates an original B-scan and a rescaled B-scan, where the B-scan was rescaled according to the example method illustrated in FIG. 2.

Referring back to FIG. 2 and also to FIG. 4, the method 200 continues with the rescaling of the distribution of signal amplitudes (step 208). The rescaling step can be performed on the filtered second pixmap by the amplitude normalization module described above. In some implementations, each A-scan signal can be rescaled based on a pixel intensity histogram. FIGS. 4A and 4B illustrate an example of this process. FIG. 4A illustrates an original A-scan 400 and a rescaled A-scan 450. FIG. 4B illustrates example B-scans before and after rescaling. In some implementations, the rescaling improves the dynamic range within the meaningful retinal signal. For example, for an 8-bit gray scale image, much of dynamic range in the original A-scan image (and pixmap) may be devoted to noise or portions of the non-retinal signal. In one example, signal levels between the 66th percentile and 99th percentile on the histogram can be rescaled across the full dynamic range (or other percentiles as described herein). For example, in an 8-bit data gray scale level, the lower 66th percentile can be set to 0 and top 1st percentile can be set to 255, with the 66th percentile to 99th percentile distributed across the dynamic range (or other percentiles as described herein). In some implementations, the lower cutoff can be determined based on the average thickness of the meaningful signal focusing on the retina. For example, if the meaningful portion of the image (e.g., the retina with a part of choroid) is about 660 μm tall and the can length is 2.0 mm, the meaningful portion of the image is roughly 33% of the image. If the meaningful portion of the image is taller, the 66th percentile to 99th percentile range can be expanded accordingly. This cutoff is commonly used on many devices for the pseudo-color visualization of OCT image data. The pixel intensities may be rescaled using the below equation:

$$I_R = \frac{I_S - noise_S}{saturation_S - noise_S} \times (saturation_O - noise_O) + noise_S \quad (6)$$

In equation 6, A and $I_R$ refer to the pixel intensity before and after signal rescaling, $saturation_O$ and $noise_O$ refer to the saturation and noise level on the original A-scan, and $saturation_S$ and $noise_S$ refer to the saturation and noise level on the smoothed A-scan profile.

FIG. 4A illustrates an original A-scan 400 and a rescaled A-scan 450 using the above process. As illustrated in the original A-scan 400, much of the dynamic range is not used—for example, few pixels include an intensity above about 150. As described above, the top 1st percentile of the intensities was set to 255 and the bottom 66th percentile was set to 0. The remaining data was distributed across the remaining dynamic range as is illustrated in the rescaled A-scan 450. FIG. 4B illustrates four cross-sectional images (B-scans). Scans 402 and 404 are unprocessed. Scans 452 and 454 are scans 402 and 404, respectively, after being rescaled using the above process. As illustrated, scans 452 and 454 provide greater detail and improved contrast when compared to the original scans 402 and 404.

Referring again to FIG. 2, the method 200 can also include normalizing the distribution of the signal amplitudes (step 210). The normalizing of the distribution of the signal amplitudes of the rescaled signal from step 208 can be performed by the quality compensation module. In some implementations, normalizing the distribution of the signal amplitudes can compensate for poor image quality. In some implementations, the distribution is normalized using a HDR process. In other implementations, the distribution can be normalized using a HM process. In some implementations, the HDR process can improve image quality by expanding the image contrast dynamic range by combining two or more images with a wide range of exposure settings. In some implementations, only a single image may be used. The single image may be divided into a plurality of channels which are individually processes and then combined to form an HDR processed image. For example, the HDR process may involve dividing the pixmap into a low level signal, a medium level signal, and a high level signal. Each of the low-level signal, medium level signal, and high level signal can be linearly scaled between the highest and lowest value within each of the respect signals. The scaled signals can then be combined to create a HDR processed image.

In some implementations, dividing an OCT image into a plurality of virtual images can include calculating four different histogram parameters of a B-scan image. The histogram parameters can include minimum, maximum, noise, and saturation levels. The minimum and maximum histogram levels can represent the lowest and the highest pixel values of the B-scan image. The noise level and the saturation level can represent the $66^{th}$ and the $99^{th}$ percentile, respectfully, of the pixel values of the B-scan image (or other percentiles as described herein). For each B-scan, the original OCT signal dataset was divided into three channels: low, medium, and high signal channels. The low signal channel ($I_{Low}$) included pixel values between minimum and low levels, the high signal channel ($I_{High}$) included pixel values between the high and saturation levels, and the medium signal ($I_{Mid}$) included pixel values between the low level and high level. The low and high levels can be defined as:

Low offset=noise+0.23×(saturation−noise),

High offset=saturation−0.067(saturation−noise) (7)

Each channel is then processed to maximize the signal dynamic range by linearly rescaling the pixel values between the lowest and the highest values within each channel to the full 8-bit gray scale range (0 to 255) in each B-scan. Intensity values outside of the defined cutoff values (lower or higher) are forced to be either 0 or 255.

Signals from all three channels can be combined to generate the final HDR dataset by calculating a weighted mean value of the three channels, as shown in equation 8. I (x, z) indicates the pixel value at position (x, z) in the processed B-scan (e.g., the xth A-scan and zth pixel in the axial direction). $c_L$, $c_M$, and $c_H$ are the weighted coefficients. The coefficients used for calculating the weighted mean can be adjusted so that the image quality can be enhanced for OCT images with poor signal strength, while preventing the images with good signal strength from becoming saturated. Example coefficients include 3.0 for $c_L$, 2.0 for $c_M$, and 1.0 for $c_H$.

$$I_{HDR}(x, y) = \frac{1}{c_L + c_M + c_H}(c_L \times I_{Low}(x, y) + c_M \times I_{Mid}(x, y) + c_H \times I_{High}(x, z)) \quad (8)$$

Figure 5:
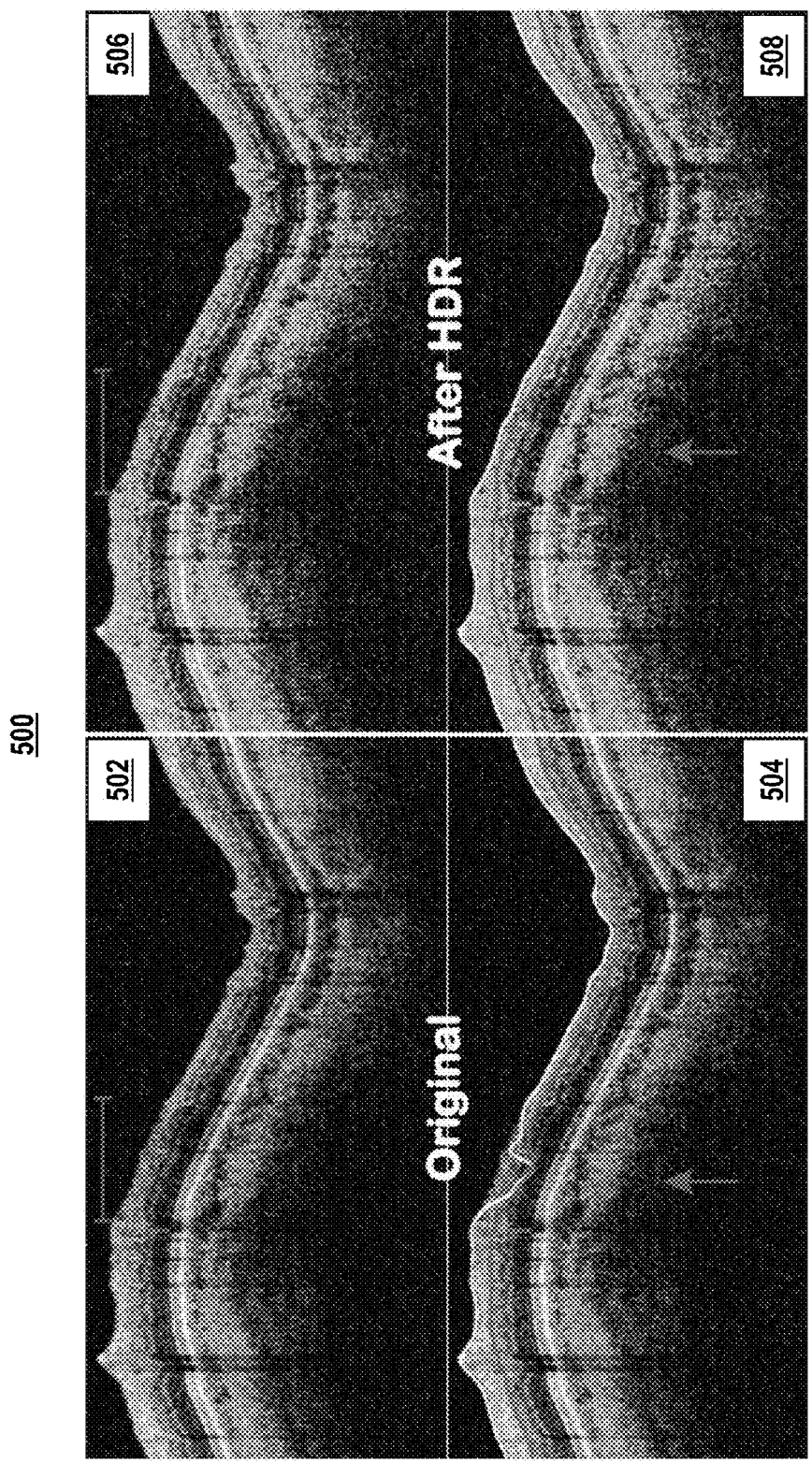
FIG. 5 illustrates two OCT images before and after HDR processing, where the OCT images were processed according to the example method illustrated in FIG. 2.

FIG. 5 illustrates two OCT images before and after HDR processing. The two original images 502 and 504 have poor signal quality when compared to the two HDR processed image 506 and 508. The improvement in the signal quality can be seen in the improvement in the contrast between adjacent retinal layers, and the increased definition between layers with high and low reflectivity. The before and after images also illustrate that the signal becomes more homogeneous.

As described above in reference to FIG. 2, in some implementations, step 210 can include normalizing the distribution of the signal amplitudes with a HM process. HM is an image processing technique to calibrate the differences in intensity contrast when capturing images with different cameras, image acquisition equipment, settings, and different light sources by matching the histogram to a reference histogram. By shaping an input image histogram to a reference histogram, the HM process can compensate for the differences in intensity and image contrast and enhance the image quality. An example HM method is discussed in relation to FIGS. 6 and 7.

Figure 6:
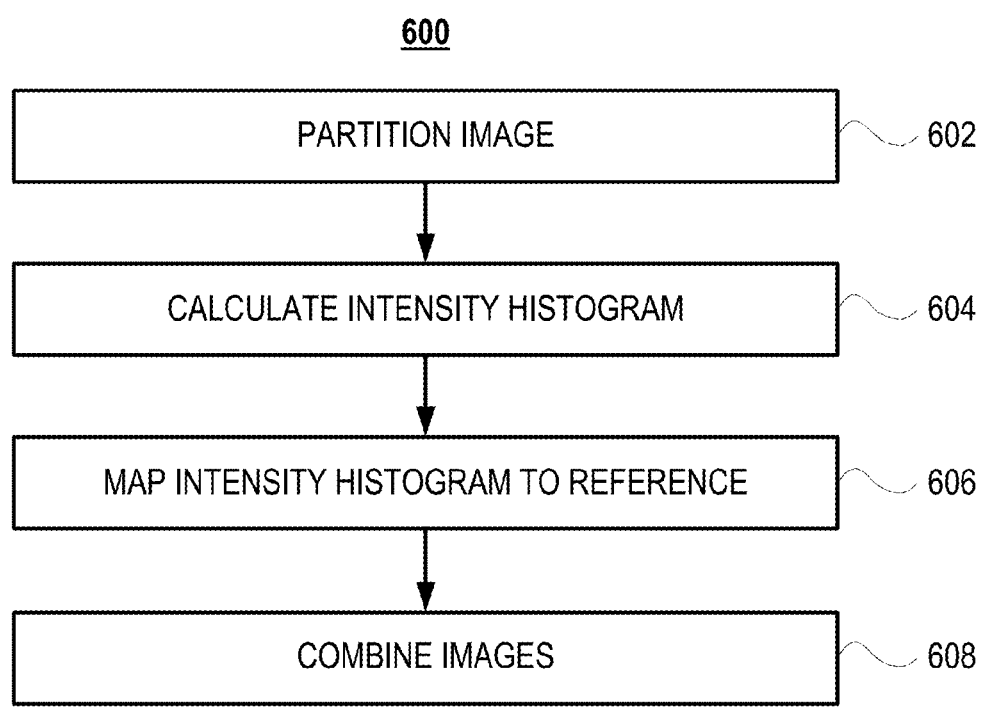
FIG. 6 illustrates a flow diagram of an example method for performing a histogram matching process according to the example method illustrated in FIG. 2.

FIG. 6 illustrates an example method 600 of performing histogram matching on an OCT image. The method 600 includes partitioning the OCT image (step 602). The method 600 also includes calculating at least one intensity histogram of the OCT image (step 604). The at least one intensity histogram can then be mapped to at least one reference intensity histogram (step 606). The mapped intensity histograms can then be combined to form a histogram matched OCT image (step 608).

Figure 7:
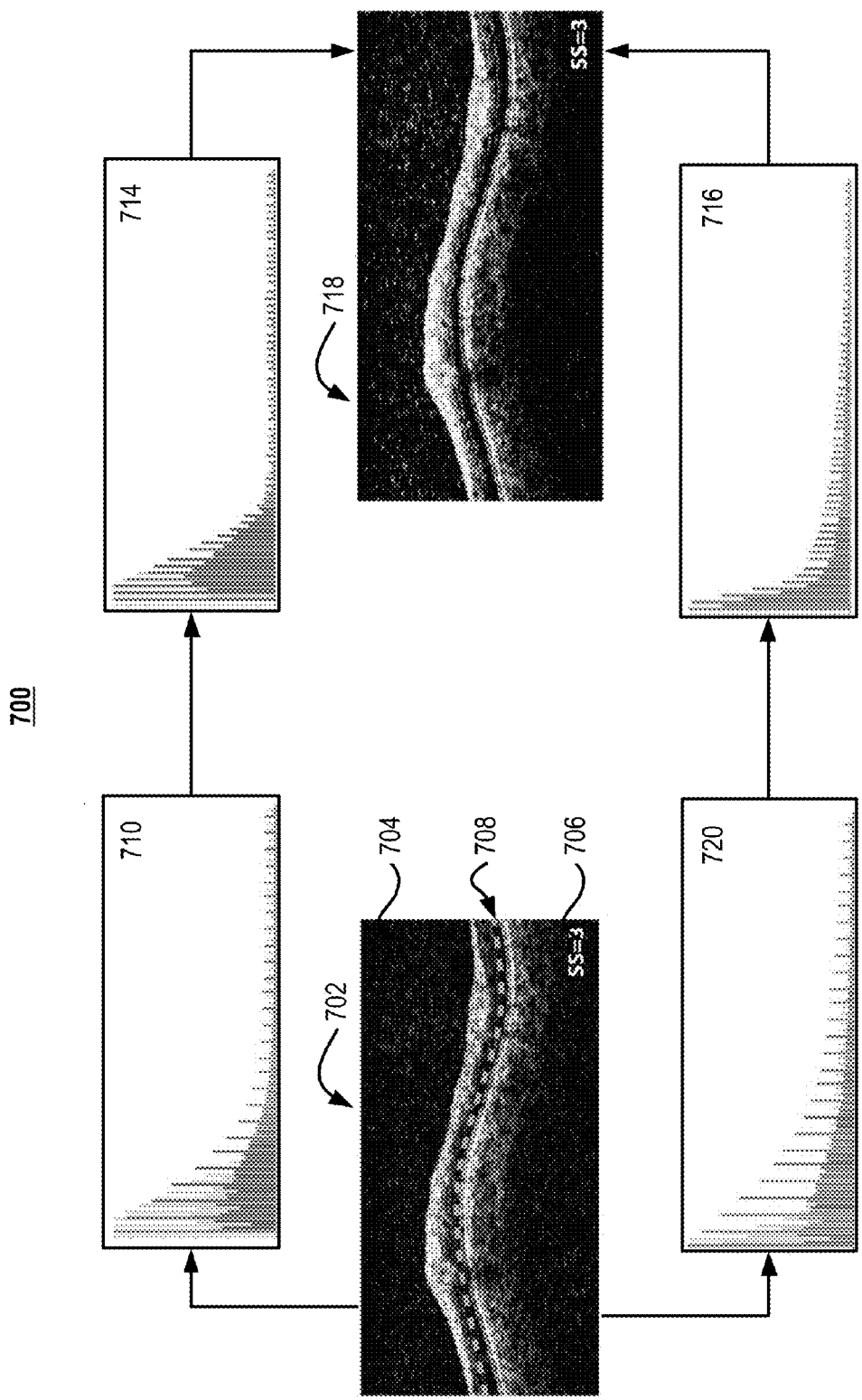
FIG. 7 illustrates an OCT image during the method illustrated in FIG. 6.

As set forth above and also referring to FIG. 7, the example method 600 can include partitioning an OCT image (step 602). FIG. 7 illustrates an OCT image during each of the steps of the method 600. FIG. 7 illustrates an example B-scan image 702 from an OCT device. As described above, the partitioning module 120 of the normalization engine 102 can receive an OCT image and partition the image. FIG. 7 illustrates a partitioning line 708, which divides the B-scan image 702 into upper and lower portions. The partitioning line 708 may divide the B-scan along the valley of the OCT signal amplitude where the amplitude is the lowest between the outer plexiform layer and the external limiting membrane. The partitioning line 708 divides the B-scan image 702 into an upper portion 704 (also referred to as an inner retinal peak) and a lower portion 706 (also referred to as an outer retinal peak).

Referring to FIG. 6, the example method 600 can also include calculating at least one intensity histogram (step 604). The intensity calculation module 124 can calculate the at least one intensity histogram of the OCT image. For example, the partitioning module 120 may partition a B-scan image received from the database 114 into upper and lower portions. The intensity calculation module 124 may generate an intensity histogram for each of the lower and upper portions. As described above, the intensity calculation module 124 may use equation 1 to generate an intensity histogram that represents the percentage of pixels from each partition at each intensity level. In some implementations, for 8-bit data the intensity levels of each B-scan are scaled between 0 and 255 prior to generating the intensity histogram. In some implementations, for 12-bit or 16-bit data the B-scan can be can be scaled to 0-4095 or 0-65535, respectively.

FIG. 7 also illustrates an example intensity histogram 710 generated form the upper portion 704, and an example intensity histogram 720 generated form the lower portion 706. In some implementations, the calculating the intensity histogram, the normalization engine 102 can calculate one or more sub-features for each of the pixels in the B-scan. Artifacts can occur in the intensity histograms because in some implementations the procedure to generate an intensity histogram can treat pixels with the same intensity as a group and may not distinguish between the pixels within the group. For example, rounding errors can artificially create intensity bins in the intensity histogram with a large number of pixels. As an example, an intensity histogram can include a plurality of "spikes," which are intensity bins with an artificially increased number of pixels. The sub-feature can enable the discernment of pixels with the same intensity, but that are in different retinal layers. The intensity histograms generated using the sub-features may better match a reference histogram.

Referring to FIG. 6, the method 600 can also include mapping at least one intensity histogram to at least one reference intensity histogram (step 606). For example, a mapping matrix can be used to convert the shape of the input histogram from the intensity calculation module 124 to the shape of the respective reference histogram. The mapping matrix may match or reduce the distance in percentile at each intensity on the histograms between reference and input histograms and is described above in relation to equation 3. FIG. 7 illustrates the generation of an upper mapped histogram 714 and a lower mapped histogram 716 by mapping of the upper intensity histogram 710 and lower intensity histogram 720 to reference histograms by the mapping module 126. In some implementations, the reference histogram used in the processing of the upper intensity histogram 710 is different than the reference histogram used in the processing of the lower intensity histogram 720. In some implementations, the reference histograms are generated from an original OCT scan with a high SS. In other implementations, a global reference histogram is generated from the mean of a plurality of OCT scans taken from a population of patients. A global reference histogram generated from a plurality of OCT scans can enable OCT scans captured at different times with different types of OCT devices to be more readily compared.

The method 600 can conclude with combination of the images formed from the mapped intensity histograms (step 608). For example, and referring to FIG. 7, the upper mapped histogram 714 and the lower mapped histogram 716 can be converted back into respective upper and lower portions of a B-scan image. The upper and lower portions of the processed B-scan can be combined to generate a histogram matched OCT image 718.

Referring again to FIG. 2, the method 200 can also include providing a normalized image (step 212). In some implementations, the normalized image may be provided to a database for storage and later retrieval. In some implementations, the normalized image may be provided to computer software for presentation local or remote to the normalization engine 102. In yet other implementations, the normalized image may be provided to an OCT comparator software program that compares a plurality of OCT images. For example, the OCT comparator software may compare the OCT images of a specific patient taken over the patient's medical history.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Computer Apparatus and Processing

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Definitions

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. All publicly available documents referenced herein, including but not limited to U.S. patents, are specifically incorporated by reference.

What is claimed:

1. A method for normalizing an image of an eye among multiple optical coherence tomography (OCT) devices comprising, in the following specified sequence:
   (a) receiving a first pixmap comprising a first plurality of pixels, wherein the first pixmap represents an image of an eye and the first pixmap has a first sample density;
   (b) normalizing a sample density;
   (c) normalizing an amount of noise using a suitable noise reduction technique;
   (d) applying a histogram matching (HM) process to normalize a distribution of signal amplitudes by:
      (i) dividing the first pixmap into a first portion and a second portion along a partitioning line;
      (ii) calculating a first histogram from the first portion of the first pixmap;
      (iii) mapping the first histogram to a first reference histogram to generate a first mapped histogram;
      (iv) calculating a second histogram from the second portion of the first pixmap;

(v) mapping the second histogram to a second reference histogram to generate a second mapped histogram; and (vi) generating a second pixmap based on a combination of the first mapped histogram and the second mapped histogram; and (e) normalizing a signal quality of the second pixmap;

wherein the sequence of steps results in a normalized image of the eye among multiple optical coherence tomography devices.

2. The method of claim 1, wherein step (b) comprises:
(i) resampling the first plurality of pixels of the first pixmap at a predetermined sampling density.

3. The method of claim 1, wherein step (c) comprises filtering the first pixmap to remove at least a portion of a noise signal in the first pixmap.

4. The method of claim 3, wherein step (d) comprises:
(i) resealing a distribution of signal amplitudes of the filtered first pixmap such that the distribution of signal amplitudes spans a substantial portion of a dynamic range of the filtered first pixmap; and
(ii) normalizing the distribution of signal amplitudes of the resealed, filtered first pixmap.

5. The method of claim 1, wherein step (d) comprises applying a high-dynamic range (HDR) process to the first pixmap.

6. The method of claim 5, wherein the HDR process further comprises:
(a) dividing the first plurality of pixels into a low level signal, a medium level signal, and a high level signal;
(b) linearly scaling each of the low level signal, the medium level signal, and the high level signal between a lowest and a highest value within each of the respective signals; and
(c) combining the linearly scaled low level, medium level, and high level signals.

7. The method of claim 1, comprising:
(a) generating an updated first portion from the first mapped histogram;
(b) generating an updated second portion from the second mapped histogram; and
(c) generating the second pixmap based on a combination of the updated first portion and the updated second portion.

8. The method of claim 1, wherein the partitioning line is a line representing a lowest intensity between an outer plexiform layer and an external limiting membrane of the eye.

9. The method of claim 1, wherein resealing the distribution of signal amplitudes further comprises:
(a) generating a histogram of pixel intensities of the first plurality of pixels;
(b) setting a portion of the first plurality of pixels below about a 66% of the histogram of pixel intensities to 0; and
(c) distributing a portion of the first plurality of pixels between about a 66 percentile and about a 99th percentile of the histogram across the substantial portion of the dynamic range.

10. The method of claim 1, wherein filtering the first pixmap further comprises applying a mask to the first pixmap, the mask comprising a smoothed copy of the first pixmap.

11. A system for normalizing an image of an eye among multiple optical coherence tomography devices comprising one or more data processors and one or more storage devices storing instructions that when executed by the one or more data processors cause the one or more data processors to:

(a) receive a first pixmap comprising a first plurality of pixels, the first pixmap representing an image of an eye and having a first sample density;

(b) generate a second pixmap comprising a second plurality of pixels by resampling the first plurality of pixels at a predetermined sampling density;

(c) filter the second pixmap to remove at least a portion of a noise signal in the second pixmap;

(d) rescale a distribution of signal amplitudes of the filtered second pixmap such that the distribution of signal amplitudes spans a substantial portion of a dynamic range of the filtered second pixmap;

(e) normalize the distribution of signal amplitudes of the rescaled, filtered second pixmap with a histogram matching (HM) process, wherein to normalize the distribution of signal amplitudes the instructions cause the one or more data processors to:
(i) divide the second pixmap into a first portion and a second portion along a partitioning line;
(ii) calculate a first histogram from the first portion of the second pixmap;
(iii) map the first histogram to a first reference histogram to generate a first mapped histogram;
(iv) calculate a second histogram from the second portion of the second pixmap;
(v) map the second histogram to a second reference histogram to generate a second mapped histogram; and
(vi) generate a third pixmap based on a combination of the first mapped histogram and the second mapped histogram; and (f) provide a normalized image of the eye based on the third pixmap.

12. The system of claim 11, wherein the instructions further cause the one or more processors to normalize the distribution of signal amplitudes by applying a high-dynamic range (HDR) process to the second pixmap.

13. The system of claim 12, wherein the HDR process further comprises:
(a) dividing the second plurality of pixels into a low level signal, a medium level signal, and a high level signal;
(b) linearly scaling each of the low level signal, the medium level signal, and the high level signal between a lowest and a highest value within each of the respective signals; and
(c) combining the linearly scaled low level, medium level, and high level signals.

14. The system of claim 11, wherein the instructions cause the one or more processors to:
(a) generate an updated first portion from the first mapped histogram;
(b) generate an updated second portion from the second mapped histograms;
(c) generate the third pixmap based on a combination of the updated first portion and the updated second portion.

15. The system of claim 11, wherein the partitioning line is a line representing a lowest intensity between an outer plexiform layer and an external limiting membrane of the eye.

16. The system of claim 11, wherein the instructions further cause the one or more processors to rescale the distribution of signal amplitudes by:
(a) generating a histogram of pixel intensities of the second plurality of pixels;

(b) setting a portion of the second plurality of pixels below about a 66th percentile of the histogram to 0; and
(c) distributing a portion of the second plurality of pixels between about a 66th percentile and about a 99th percentile of the histogram across the substantial portion of the dynamic range.

17. The system of claim 11, wherein the instructions further cause the one or more processors to filter the second pixmap by applying a mask to the second pixmap, the mask comprising a smoothed copy of the second pixmap.

18. The system of claim 11, wherein the instructions further cause the one or more processors to resample the first sample density by up scaling the first sample density.

* * * * *

UNITED STATES PATENT AND TRADEMARK OFFICE
CERTIFICATE OF CORRECTION

PATENT NO. : 9,844,315 B2
APPLICATION NO. : 14/877178
DATED : December 19, 2017
INVENTOR(S) : Chieh-Li Chen et al.

Page 1 of 1

It is certified that error appears in the above-identified patent and that said Letters Patent is hereby corrected as shown below:

In the Specification

In Column 1, after Line 18, insert the following paragraphs:
--STATEMENT REGARDING FEDERALLY SPONSORED RESEARCH
This invention was made with government support under grant numbers EY013178 and EY008098 awarded by the National Institutes of Health. The government has certain rights in the invention.--

Signed and Sealed this
Ninth Day of July, 2019

Andrei Iancu
*Director of the United States Patent and Trademark Office*